United States Patent [19]

Aldcroft et al.

[11] Patent Number: 4,956,167
[45] Date of Patent: Sep. 11, 1990

[54] SILICAS

[75] Inventors: Derek Aldcroft, South Wirral; John R. Newton, Cheshire; James P. Quinn, Birkenhead; Peter W. Stanier, Cheshire, all of United Kingdom

[73] Assignee: Unilever Patent Holdings B.V., Rotterdam, Netherlands

[21] Appl. No.: 327,392

[22] Filed: Mar. 22, 1989

Related U.S. Application Data

[63] Continuation of Ser. No. 19,859, Feb. 27, 1987, abandoned.

[30] Foreign Application Priority Data

Feb. 28, 1986 [GB] United Kingdom ............... 8604985

[51] Int. Cl.$^5$ ..................... C01B 33/18; A01K 1/16
[52] U.S. Cl. ................................. 423/339; 423/335; 424/49
[58] Field of Search ................ 423/335, 338, 339; 424/49

[56] References Cited

U.S. PATENT DOCUMENTS

| 3,960,586 | 6/1976 | Wason | 106/288 B |
| 3,977,893 | 8/1976 | Wason | 106/288 B |
| 4,100,264 | 7/1978 | Pader | 424/49 |
| 4,122,161 | 10/1978 | Wason | 424/49 |
| 4,153,680 | 5/1979 | Seybert | 424/49 |
| 4,421,527 | 12/1983 | Wason | 423/339 |
| 4,581,217 | 4/1986 | Shinpo et al. | 423/339 |
| 4,590,052 | 5/1986 | Chevallier et al. | 423/239 |

FOREIGN PATENT DOCUMENTS

| 1189681 | 2/1985 | Canada . |
| 1183672 | 12/1985 | Canada . |
| 0139754 | 8/1985 | European Pat. Off. . |
| 0143848 | 12/1985 | European Pat. Off. . |
| 1467019 | 1/1969 | Fed. Rep. of Germany . |
| 2446038 | 4/1975 | Fed. Rep. of Germany . |
| 1416139 | 12/1975 | United Kingdom . |
| 1447663 | 8/1976 | United Kingdom . |
| 1482355 | 8/1977 | United Kingdom . |
| 1501905 | 2/1978 | United Kingdom . |
| 1532398 | 11/1978 | United Kingdom . |
| 2038303 | 7/1980 | United Kingdom . |

*Primary Examiner*—Robert L. Stoll
*Assistant Examiner*—Lori F. Cuomo
*Attorney, Agent, or Firm*—Cushman, Darby & Cushman

[57] ABSTRACT

An amorphous silica, especially precipitated silica, suitable for use in toothpastes, has a high abrasivity represented by a perspex abrasion value in the range from about 23 to about 35.

2 Claims, No Drawings

SILICAS

This is a continuation of application No. 019,859, filed Feb. 27, 1987, now abandoned.

FIELD OF THE INVENTION

This invention relates to synthetic amorphous silicas, especially precipitated silicas, of use, for example, as abrasive agents in toothpaste compositions.

BACKGROUND TO THE INVENTION

Toothpaste compositions are well characterised in the literature and many compositions are disclosed in patent specifications and other literature. Toothpaste compositions contain a number of specific components for example abrasive agents, fluoride sources, binders, preservatives, humectants, anti plaque agents, colouring agents, water, flavour and other optional ingredients. Of these components the abrasive agent is required to provide the appropriate cleaning and plaque removal without subjecting the tooth itself to excessive abrasion. Typically a toothpaste composition will contain from about 5% to about 50% preferably up to about 30% by weight of abrasive. Commonly used abrasives are aluminas, calcium carbonates and calcium phosphates. More recently synthetic silicas have been adopted because of their efficient cleaning, compatibility with other ingredients and their physical properties.

GENERAL DESCRIPTION OF THE INVENTION

The silicas of the invention provide a novel range of properties, combining remarkedly high levels of abrasivity coupled with low surface areas and an unusually high degree of openness of structure as defined by porosity measurements. In particular, such high levels of abrasivity have not been found previously from a precipitate route.

The silicas of the invention are capable of providing high levels of abrasion even at relatively low particle sizes i.e. 3 to 8 micron range and/or levels of moisture from about 1% to about 35%. Abrasive materials can also be obtained at particle sizes beyond the stated upper limit but they are not suitable for use in toothpastes because of the unacceptable mouth feel of the coarser particles.

In general, characterisation of the pore structure of silicas containing higher levels of openness and wider pores by nitrogen adsorption techniques is not meaningful because this technique is useful only for pores up to about 30 nm diameter. To measure the full range of porosity present in such materials it is necessary to employ alternative procedures, for example oil absorption or mercury porosimetry. Since the products of this invention have considerable pore structure in excess of 30 nm it is necessary to define them by means of such techniques.

The invention provides an amorphous silica, preferably a precipitated silica, having (i) a surface area in the range from about 10, preferably from about 50, to about $450 m^2/g$, usually about 200 to about $400 m^2/g$, (ii) a weight mean particle size in the range 3 microns to 20 microns, preferably above 5 micron and below 15 microns, (iii) a perspex abrasion value in the range from about 23 to about 35, and, optionally for precipitated silicas, (iv) an oil absorption in the range from about 60 to about 110 cc/100 g, preferably up to about 95 cc/100 g. These perspex abrasion values correspond to Radioactive Dentine Abrasion values of 150 to 300.

The invention extends to a method of reacting a silicate solution and acid solution in the presence of electrolyte to provide precipitated silicas according to the invention.

The invention includes a method of preparing an amorphous precipitated silica, suitable for use as a toothpaste abrasive, and having (i) a surface area in the range from about 10 to about $450 m^2/g$,
(ii) a weight mean particle size in the range from about 3 to about 20 microns,
(iii) a perspex abrasion value in the range from about 23 to about 35, and optionally,
(iv) an oil absorption in the range from about 60 to about 110 cc/100 g which is produced by the reaction of sodium silicate, having a silica:$Na_2O$ ratio in the range from 1.8 to 3.5:1, with mineral acid, with the concentration and volume of the reactants controlled to give a reaction in the pH range from about 10 to about 10.5, in the presence of a water soluble electrolyte comprising a cation selected from the group comprising aluminium, magnesium, calcium, sodium and potassium with an associated anion selected from the group comprising bromide, carbonate, chloride, nitrate, acetate and sulphate wherein the electrolyte:silica weight ratio is from about 0.1 to 1 to about 2 to 1, the precipitation reaction being performed in the temperature range of about 95° C. to about 100° C.

Optionally the reaction medium is subjected to a hydrothermal ageing step during the final acid addition step to provide materials with lower surface areas.

Standard Procedures

The silicas of the invention are defined in terms of their physical and chemical properties. The standard test methods used for these properties are:

(i) Surface Area:

Surface area is determined using standard nitrogen adsorption methods of Brunauer, Emmett and Teller (BET), using a single point method with a Sorpty 1750 apparatus supplied by Carlo Erba company of Italy. The sample was outgassed under vacuum at 270° C. for 1 hour before measurement.

(ii) Oil Absorption:

The oil absorption is determined by the ASTM spatula rub-out method (American Society of Test Material Standards D, 281).

The test is based upon the principle of mixing linseed oil with a silica by rubbing with a spatula on a smooth surface until a stiff putty-like paste is formed which will not break or separate when it is cut with the spatula. The volume of oil used is then put into the following equation:

$$\text{Oil absorption} = \frac{cm^3 \text{ oil absorption} \times 100}{\text{wt. of silica sample in gms}}$$

$$= cm^3 \text{ oil}/100 \text{ g silica}$$

(iii) Weight Mean Particle Size:

The weight mean particle size of the silicas was determined with the aid of a Malvern Particlesizer, Model 3600 E. This instrument, made by Malvern Instruments, Malvern, Worcestershire uses the principle of Fraunhöffer diffraction utilising a low power He/Ne laser. Before measurement the sample was dispersed ultrasonically in water for a period of 7 minutes to form an aqueous suspension.

(iv) Perspex Abrasion Value:

This test is based upon a toothbrush head brushing a perspex plate in contact with a suspension of the silica in a sorbitol/glycerol mixture. Normally the slurry composition is as follows:

|  |  |
| --- | --- |
| Silica | 2.5 grams |
| Glycerol | 10.0 grams |
| Sorbitol Syrup* | 23.0 grams |

*Syrup contains 70% sorbitol/30% water.

All components are weighed into a beaker and dispersed for 2 minutes at 1500 rpm using a simple stirrer. A 110 mm×55 mm×3 mm sheet of standard clear Perspex is used for the test, supplied by Imperial Chemical Industries Plc under code 000.

The test is carried out using a modified Wet Paint Scrub Tester produced by Research Equipment Limited, Wellington Road, Hampton Hill, Middlesex. The modification is to change the holder so that a toothbrush can be used instead of a paint brush. In addition a weight of 14 ozs is attached to the brush to force the brush onto the perspex plate.

A Galvanometer is calibrated using a 45° Plaspec gloss head detector and a standard (50% gloss) reflecting plate. The Galvanometer reading is adjusted to a value of 50 under these conditions. The reading of the fresh perspex plate is then carried out using the same reflectance arrangement.

The fresh piece of perspex is then fitted into a holder. Two mls of the dispersed silica, sufficient to lubricate fully the brushing stroke, is placed on the plate and the brush head lowered onto the plate. The machine is switched on and the plate subjected to three hundred strokes of the weighted brush head. The plate is removed from the holder and all the suspension is washed off. It is then dried and re-measured for its gloss value. The abrasion value is the difference between the unabraded value and the value after abrasion.

This test procedure, when applied to known abrasives, gave the following values:

|  | Perspex abrasion value |
| --- | --- |
| Calcium carbonate (15 micron) | 32 |
| Silica xerogel (10 micron) prepared by UK 1264292 method | 25 |
| Alumina trihydrate (Gibbsite) (15 micron) | 16 |
| Calcium pyrophosphate (10 micron) | 14 |
| Dicalcium phosphate dihydrate (15 micron) | 7 |

(v) Loose Bulk Density:

Loose bulk density is determined by weighing approximately 180 ml of silica into a dry 250 ml measuring cylinder, inverting the cylinder ten times to remove air pockets and reading the final settled volume.

$$\text{Loose bulk density} = \frac{\text{Weight}}{\text{Volume}} \times 1000 \text{ g/l}$$

(vi) Electrolyte Levels:

Sulphate is determined gravimetrically by hot water extraction of the silica, followed by precipitation as barium sulphate. Chloride is determined by hot water extraction of the silica, followed by titration with standard silver nitrate solution using potassium chromate as indicator (Mohr's method).

(vii) Moisture Loss at 105° C.:

Moisture loss is determined by the loss in weight of a silica when dried to constant weight in an electric oven at 105° C.

(viii) Ignition Loss at 1000° C.:

Ignition loss is determined by the loss in weight of a silica when ignited in a furnace at 1000° C. to constant weight.

(ix) pH:

This measurement is carried out on a 5% w/w suspension of the silica in boiled demineralised water ($CO_2$ free)

(x) Filter Cake Ignition Loss:

Filter cake ignition loss is determined by the loss in weight of a silica filter cake when ignited in a furnace at 1000° C. to constant weight.

(xi) Radioactive Dentine Abrasion Test (RDA):

The procedure follows the method for assessment of dentifrice abrasivity recommended by the American Dental Association (Journal of Dental Research 55 (4) 563, 1976). In this procedure extracted human teeth are irradiated with a neutron flux and subjected to a standard brushing regime. The radioactive phosphorous 32 removed from the dentin in the roots is used as the index of the abrasion of the dentifrice tested. A reference slurry containing 10 g of calcium pyrophosphate in 15 ml of 0.5% aqueous solution of sodium carboxymethyl cellulose is also measured and the RDA of this mixture is arbitrarily taken as 100. The precipitated silica to be tested is prepared as a suspension at the same concentration as the pyrophosphate and submitted to the same brushing regime.

The RDA's obtained are quoted for a number of the examples of silicas prepared within the present invention. By examining a range of silicas, including those described in the present invention, it has been found there is a correlation between plastics abrasion value and RDA over fifteen samples with a correlation coefficient of 0.91 (confidence 99%).

(xii) Mercury intrusion volume:

Mercury intrusion volumes are determined (in cc/g) by standard mercury intrusion procedures using a Micromeritics Autopore 9220 mercury porosimeter. The pore radius is calculated from the Washburn equation using values of surface tension for mercury of 485 dynes/cm and contact angle cf 140°.

Prior to measurement the sample was outgassed at room temperature to a pressure of 50 microns of mercury. The mercury intrusion volume recorded is that occurring over the range of calculated pore diameters of 0.05 to 1.0 micron.

(xiii) Refractive index (RI)/transmission:

The sample silica was dispersed in a range of water/sorbitol (70% syrup) mixtures. The RI for each dispersion was measured together with the percentage transmission using illumination of 589 nm and water as a blank. The RI of the silica is taken to correspond to the maximum transmission and presentation of the transmission against RI graphically allows the transmission over a range of RI to be readily demonstrated.

DESCRIPTION OF THE INVENTION

Examples of the preparation of precipitated silicas will now be given to illustrate but not limit the invention. Example 11 is included as a comparison to show the criticality of the reaction temperature on the abrasivity of the resulting silica.

A heated stirred reaction vessel was used for the silicate/acid reaction.

The solutions used in the process were as follows:
(i) Sodium silicate solutions having a $SiO_2:Na_2O$ ratio in the range of 1.9 to 3.4:1.
(ii) A sulphuric acid solution of specific gravity 1.11 (16.1% W/W solution) to 1.185 (25.9% W/W solution).
(iii) An electrolyte solution as defined in each example.

The following procedure was adopted in the preparation of the precipitated silicas. Values of reactant concentrations and volumes, and reaction temperatures are given in Table 1.

(A) liters of water were placed in the vessel together with (B) liters of electrolyte solution and (C) liters of the sodium silicate solution. This mixture was then stirred and heated to (E)° C.

The sodium silicate ((D) liters) and sulphuric acid ((F) liters) solutions were then added simultaneously over a period of about 20 minutes with stirring while maintaining the temperature at (E)° C. The flow rates of the silicate and acid solutions were uniform throughout the addition period to ensure that a constant pH was maintained in the vessel. (G) liters of electrolyte solution was then added over a period of (H) minutes with continued mixing at (E)° C. Sulphuric acid solution was then added over a period of 10 minutes with continued mixing to reduce the pH of the liquid to the range of 3.0 to 3.5. During this addition of acid the temperature was maintained. Optionally a hydrothermal ageing step can be introduced during the acid addition if materials with lower surface areas are required. This is illustrated by Examples 5, 13, 14, 15, 16, 17 and 18. The resultant slurry was then filtered and washed with water to remove excess electrolyte. Typically, for a toothpaste application, the residual electrolyte would be less than 2% on a dry weight basis.

After washing, the filter cake, which had a moisture content of (J)%, was dried and comminuted to the desired particle size range. Alternatively the filter cake can be hot air milled without drying to the desired particle size range and this procedure was used in Examples 3, 4 and 5.

The precipitated silica obtained had the properties, expressed on a dry weight basis, as listed in Table II.

The precipitated silicas prepared as described provided satisfactory cleaning properties for the toothpastes in which they were incorporated. The toothpastes had commercially suitable properties for stability and usage The major outlet for the use of these silicas is in opaque dentrifices since the percentage transmission (589 nm) of the silicas of the invention has a maximum value of about 35% over the refractive index range of 1.433 to 1.445. Typical formulations using the silicas of this invention are listed below.

| OPAQUE WHITE DENTAL CREAMS | | | |
|---|---|---|---|
| FORMULATION 1 | % | FORMULATION 2 | % |
| Sorbosil TC10 | 12.0 | Sorbosil TC10 | 8.0 |
| Silica of invention | 8.0 | Silica of invention | 14.0 |
| Xanthan Gum | 1.0 | Sodium Carboxymethyl Cellulose | 0.9 |
| Sorbitol, 70% non-crystallisable | 40.0 | Sorbitol, 70% non-crystallisable | 40.0 |
| Sodium Lauryl Sulphate | 1.5 | Polyethylene Glycol 1500 | 5.0 |
| Sodium Monofluorophosphate | 0.8 | Sodium Lauryl Sulphate | 1.5 |
| Flavour | 1.0 | Sodium Monofluorophosphate | 0.8 |
| Saccharin | 0.2 | Flavour | 1.0 |
| Titanium Dioxide | 1.0 | Saccharin | 0.2 |
| Water and Minor Ingredients | to 100 | Titanium Dioxide | 1.0 |
| Properties - Initial | | Water and Minor Ingredients | to 100 |
| Density @ 25° C. 1.36 gml$^{-1}$ | | Properties - Initial | |
| RDA 100 | | Density @ 25° C. 1.33 gml$^{-1}$ | |
| | | RDA 150 | |

Sorbosil TC10 is a thickening silica obtainable from Crosfield Chemicals of Warrington, England.

TABLE I

| Example No. | 1 | 2 | 3 | 4 | 5* | 6 | 7 | 8 | 9 | 10 | 11 |
|---|---|---|---|---|---|---|---|---|---|---|---|
| Vessel cap. (L) | 325 | 325 | 325 | 325 | 325 | 64 | 325 | 64 | 64 | 325 | 325 |
| Electrolyte used | NaCl | NaCl | NaCl | NaCl | NaCl | NaCl | CaCl$_2$ | NaNO$_3$ | Sodium acetate | NaCl | NaCl |
| Concn. of electrolyte (% w/w) | 20 | 20 | 20 | 20 | 20 | 25 | 36.3 | 30.4 | 29.8 | 25 | 25 |
| Silicate ratio SiO$_2$/Na$_2$O by wt. | 3.40 | 3.30 | 3.32 | 3.30 | 3.40 | 1.90 | 3.34 | 3.38 | 3.36 | 3.34 | 3.37 |
| SiO$_2$ Concn. in sodium silicate (% w/) | 17.41 | 16.59 | 16.73 | 16.67 | 16.66 | 15.73 | 16.47 | 16.80 | 17.10 | 16.47 | 16.72 |
| Acid concn. (% w/w) | 17.3 | 17.1 | 16.9 | 17.3 | 17.4 | 24.3 | 17.2 | 17.1 | 17.1 | 17.2 | 16.9 |
| Water vol. (A) L | 64 | 69 | 126 | 86 | 86 | 21 | 116 | 22.4 | 23.3 | 116 | 116 |
| Vol. of electrolyte (B) L | 40 | 13.5 | 24 | 0 | 0 | 3.3 | 11.5 | 3.3 | 3.3 | 17 | 17 |
| Silicate vol. (C) L | 0 | 0 | 0 | 0 | 0 | 0.2 | 1 | 0.2 | 0.2 | 1 | 1 |
| Silicate vol. (D) L | 91 | 114 | 113 | 95.5 | 95.5 | 20.2 | 104 | 19.7 | 19.2 | 104 | 103 |
| Temperature °C. (E) | 99 | 98 | 98 | 98 | 98 | 98 | 98 | 98 | 98 | 98 | 90 |
| Acid vol. (F) L | 35.5 | 44 | 43.5 | 9.5 | 9 | 8.8 | 38.5 | 7.7 | 7.4 | 38.5 | 40 |
| Electrolyte vol. (G) L | 0 | 0 | 0 | 82 | 82 | 0 | 0 | 0 | 0 | 0 | 0 |
| Time (H) minutes | 0 | 0 | 0 | 10 | 10 | 0 | 0 | 0 | 0 | 0 | 0 |

*Example 5 was hydrothermally aged for 120 minutes at pH 8 to 9.

TABLE 2

| Example No. | 1 | 2 | 3 | 4 | 5 | 6* | 7 | 8 | 9 | 10 | 11 |
|---|---|---|---|---|---|---|---|---|---|---|---|
| Cake ignition loss @ 1000° C. % W/W (J) | 27.3 | 36.9 | 38.0 | 47.2 | 64.4 | 41.5 | 65.8 | 58.7 | 38.2 | 31.6 | 65.3 |
| Surface area | 106 | 120 | 229 | 396 | 59 | 372 | 248 | 266 | 72 | 230 | 327 |

TABLE 2-continued

| Example No. | 1 | 2 | 3 | 4 | 5 | 6* | 7 | 8 | 9 | 10 | 11 |
|---|---|---|---|---|---|---|---|---|---|---|---|
| ($m^2g^{-1}$) | | | | | | | | | | | |
| Oil absorption ($cm^3/100$ g) | 60 | 65 | 95 | 90 | 95 | 61 | 82 | 75 | 75 | 59 | 180 |
| Weight mean particle size (micron) | 7.5 | 6.0 | 16.8 | 11.2 | 12.0 | 5.6 | 9.2 | 5.8 | 6.9 | 8.2 | 12.2 |
| Plastic abrasion value | 30 | 31 | 23 | 27 | 26 | 30 | 28 | 29 | 31 | 25 | 15 |
| Loose bulk density ($g.l^{-1}$) | 403 | 332 | 336 | 352 | 338 | 316 | 183 | 225 | 260 | 408 | 183 |
| RDA | 251 | 233 | 188 | 241 | 216 | NM | 145 | NM | NM | 152 | 80 |
| Electrolyte level ($SO_4^=$) (% W/W) | Tr | Tr | Tr | 0.36 | 0.26 | 0.05 | 4.53 | 0.03 | 0.01 | Tr | 0.07 |
| Electrolyte level ($Cl^-$) (% W/W) | 0.10 | 0.06 | 0.16 | 0.10 | 0.21 | 0.19 | 0.12 | 0.06 | 0.06 | 0.08 | 0.06 |
| Moisture loss @ 105° C. (%) | 2.5 | 3.1 | 22.4 | 24.0 | 27.0 | 3.1 | 5.5 | 2.8 | 1.8 | 7.7 | 3.8 |
| Ignition loss @ 1000° C. (% W/W) | 6.9 | 7.4 | 26.8 | 28.4 | 30.3 | 7.7 | 12.4 | 7.4 | 5.8 | 12.0 | 9.0 |
| pH | 7.7 | 7.4 | 6.5 | 7.3 | 6.7 | 6.1 | 6.3 | 6.8 | 7.1 | 6.9 | 7.1 |

Tr = trace
NM = not measured
*Example 6 product had a mercury intrusion volume of 0.31 cc/g

TABLE 3

| Example No. | 12 | 13 | 14 | 15 | 16 | 17 | 18 |
|---|---|---|---|---|---|---|---|
| Vessel Capacity L | 64 | 64 | 64 | 64 | 64 | 64 | 64 |
| Electrolyte used | NaCl | NaCl | NaCl | NaCl | NaCl | NaCl | NaCl |
| Concentration of Electrolyte (% w/w) | 25 | 25 | 25 | 25 | 25 | 25 | 25 |
| Silicate ratio $SiO_2$/$Na_2O$ by wt | 3.26 | 3.26 | 3.26 | 3.26 | 3.26 | 3.26 | 3.37 |
| $SiO_2$ concentration in sodium silicate (% w/w) | 16.46 | 16.46 | 16.46 | 16.46 | 16.46 | 16.46 | 16.85 |
| Acid concentration (% w/w) | 17.1 | 17.1 | 17.1 | 17.1 | 17.1 | 17.1 | 16.9 |
| Water Volume (A) L | 22.1 | 22.1 | 22.1 | 22.1 | 22.1 | 22.1 | 22.5 |
| Volume of electrolyte (B) L | 3.3 | 3.3 | 3.3 | 3.3 | 3.3 | 3.3 | 3.3 |
| Silicate Volume (C) L | 0.2 | 0.2 | 0.2 | 0.2 | 0.2 | 0.2 | 0.2 |
| Silicate Volume (D) L | 20 | 20 | 20 | 20 | 20 | 20 | 19.6 |
| Temperature °C. (E) | 98 | 98 | 98 | 98 | 98 | 98 | 98 |
| Acid Volume (F) L | 7.6 | 7.6 | 7.6 | 7.6 | 7.6 | 7.6 | 7.7 |
| Electrolyte Volume (G) L | 0 | 0 | 0 | 0 | 0 | 0 | 0 |
| Time minutes (H) | 0 | 0 | 0 | 0 | 0 | 0 | 0 |
| Time of hydrothermal ageing @ pH 8-9 (mins) | 0 | 5 | 10 | 20 | 40 | 60 | 90 |

TABLE 4

| Example No. | 12 | 13 | 14 | 15 | 16 | 17 | 18 |
|---|---|---|---|---|---|---|---|
| Cake ignition loss @ 1000° C. % (w/w) (J) | 40.5 | 38.7 | 40.3 | 41.7 | 42.4 | 40.7 | 40.4 |
| Surface Area ($m^2g^{-1}$) | 220 | 105 | 90 | 41 | 14 | 8 | 8 |
| Oil Absorption ($cm^3/100$ g) | 86 | 100 | 105 | 110 | 100 | 110 | 92 |
| Weight mean particle size (microns) | 6.6 | 10.1 | 8.7 | 9.6 | 8.5 | 9.1 | 7.5 |
| Plastic abrasion value | 26 | 31 | 29 | 30 | 30 | 30 | 27 |
| Loose bulk density ($g.l^{-1}$) | 380 | 452 | 410 | 429 | 405 | 436 | 400 |
| Mercury intrusion volume (cc $g^{-1}$) | 0.95 | 0.22 | NM | 0.21 | 0.18 | NM | NM |
| Electrolyte level ($SO_4^=$) (% w/w) | 0.47 | 0.06 | 0.12 | 0.11 | 0.07 | 0.10 | 0.01 |
| Electrolyte level ($Cl^-$) (% w/w) | 0.13 | 0.09 | 0.12 | 0.09 | 0.13 | 0.09 | 0.13 |
| Moisture loss @ 105° C. (% w/w) | 5.4 | 2.1 | 2.1 | 2.1 | 1.7 | 2.0 | 2.0 |
| Ignition loss @ 1000° C. (% w/w) | 9.5 | 6.3 | 6.4 | 6.4 | 5.9 | 6.1 | 6.2 |
| pH | 6.3 | 6.8 | 6.7 | 6.7 | 7.0 | 7.0 |

We claim:

1. A method of preparing an amorphous precipitated silica, suitable for use as a toothpaste abrasive, and having (i) a BET surface area in the range from about 10 to about 450 pl m$^2$/g, (ii) a weight mean particle size in the range from about 3 to about 20 microns, and (iii) a perspex abrasion value in the range from about 23 to about 35, which is produced by the reaction of sodium silicate, having a silica:Na$_2$O ratio in the range from 1.8 to 3.5:1, with mineral acid at a temperature of about 95° C. to 100° C., with the concentration and volume of the reactants controlled to give a reaction in the pH range from about 10 to about 10.5, in the presence of a water soluble electrolyte comprising a cation selected from the group comprising aluminium, magnesium, calcium, sodium and potassium with an associated anion selected from the group comprising bromide, carbonate, chloride, nitrate, acetate and sulphate wherein the electrolyte:silica weight ratio is from about 0.1 to 1 to about 2 to 1, adding mineral acid to lower the pH to the range of 3.0–3.5, while at least maintaining the reaction temperature and thereafter filtering the resultant slurry and recovering the precipitated silica.

2. A method according to claim 1 wherein the reaction medium is subjected to a hydrothermal ageing step during the acid addition which lowers the pH to the range of 3.0–3.5.

* * * * *